US00PP13990P39

(12) United States Plant Patent
Zipperer, III

(10) Patent No.: US PP13,990 P3
(45) Date of Patent: Jul. 22, 2003

(54) GLADIOLUS PLANT NAMED 'GEORGIA PEACH'

(76) Inventor: John O. Zipperer, III, Urbanizacion Campo Alegre, #99 El Gorrion, Quito (EC)

( * ) Notice: Subject to any disclaimer, the term of this patent is extended or adjusted under 35 U.S.C. 154(b) by 0 days.

(21) Appl. No.: 09/745,086

(22) Filed: Dec. 20, 2000

(65) Prior Publication Data

US 2002/0002721 P1 Jan. 3, 2002

(51) Int. Cl.[7] ..... A01H 5/00
(52) U.S. Cl. ..... Plt./301
(58) Field of Search ..... Plt./301

(56) References Cited

PUBLICATIONS

U.S. patent application Ser. No. 09/742,726, Zipperer, III, filed Dec. 20, 2000.

*Primary Examiner*—Bruce R. Campell
*Assistant Examiner*—Annette H. Para
(74) *Attorney, Agent, or Firm*—Hahn Loeser & Parks LLP; Laura G. Barrow

(57) ABSTRACT

A new and distinct gladiolus cultivar, designated 'Georgia Peach', shown and described. Compared to the Dr. Magee variety, the 'Georgia Peach' cultivar produced four to five more flowers per stem, is six to eight inches taller, and will maintain three to four more flowers in open bloom. The 'Georgia Peach' cultivar is able to maintain up to seven to eight flowers in open bloom simultaneously, beginning with a tight cut stem.

5 Drawing Sheets

The present invention comprises a new and distinct cultivar of a *Gladiolus l.* referred to by the cultivar name 'Georgia Peach'.

BRIEF DESCRIPTION OF THE PHOTOGRAPHS

ASEXUAL REPRODUCTION

The new cultivar was originated by the Applicant in a controlled proprietary breeding program in Ft. Myers, Fla. wherein selected gladiolus varieties were crossed. The female parent was a gladiolus variety named 'Dr. Magee' (unpatented), characterized in part by having a small pink bloom, a short stem having a short flower head, and high resistance to Fusarium fungi species. The male parent was a red gladiolus variety named 'T-111' (unpatented), characterized by having a long head, high bloom count, and good stem production. The seeds were planted in Ft. Myers, Fla., and the selection of 'Georgia Peach' cultivar was made in spring 1988. Asexual reproduction of the 'Georgia Peach' cultivar was achieved in Ft. Myers, Fla. by collecting cormels from the first corm. All subsequent asexual reproductions of the 'Georgia Peach' are true to the original variety.

BOTANICAL DESCRIPTION

Figure 1:
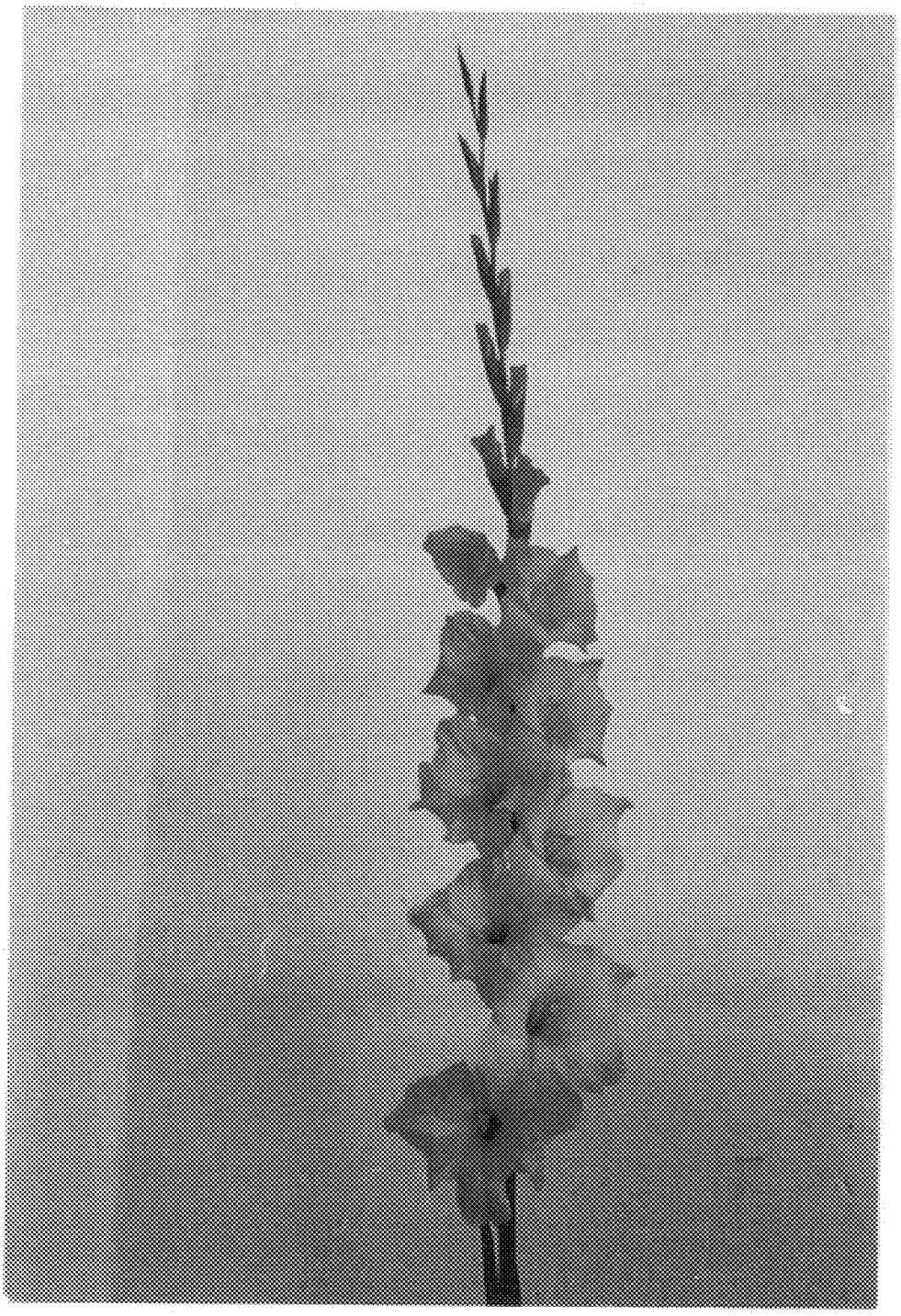
FIG. 1 is a photograph of a 'Georgia Peach' cultivar plant in bloom.

The accompanying color photograph (FIG. 1) shows the inflorescence and various stages of blooming of the 'Georgia Peach' cultivar plant.

The following botanical description of the 'Georgia Peach' cultivar was observed when the plant was 60 days old grown under the following conditions in Ecuador:

1) Twelve-hour daylight days with high light intensity;
2) Temperatures: 58–60° F. (low's) and 69–75° F. (high's);
3) Humidity: 50–55%.
4) Rainfall: 2–3 inches/month.

All color descriptions with respect to parts of the cultivar, where color is a distinguishing feature, are made to The Royal Horticultural Society Colour Chart, except where terms of ordinary usage and dictionary meaning are used. Color observations with respect to the RHS Colour Chart were made in the Netherlands under similar environmental conditions as described above, but at increased day lengths of 12 to 17 hours and 50% to 65% humidity.

Figure 2:
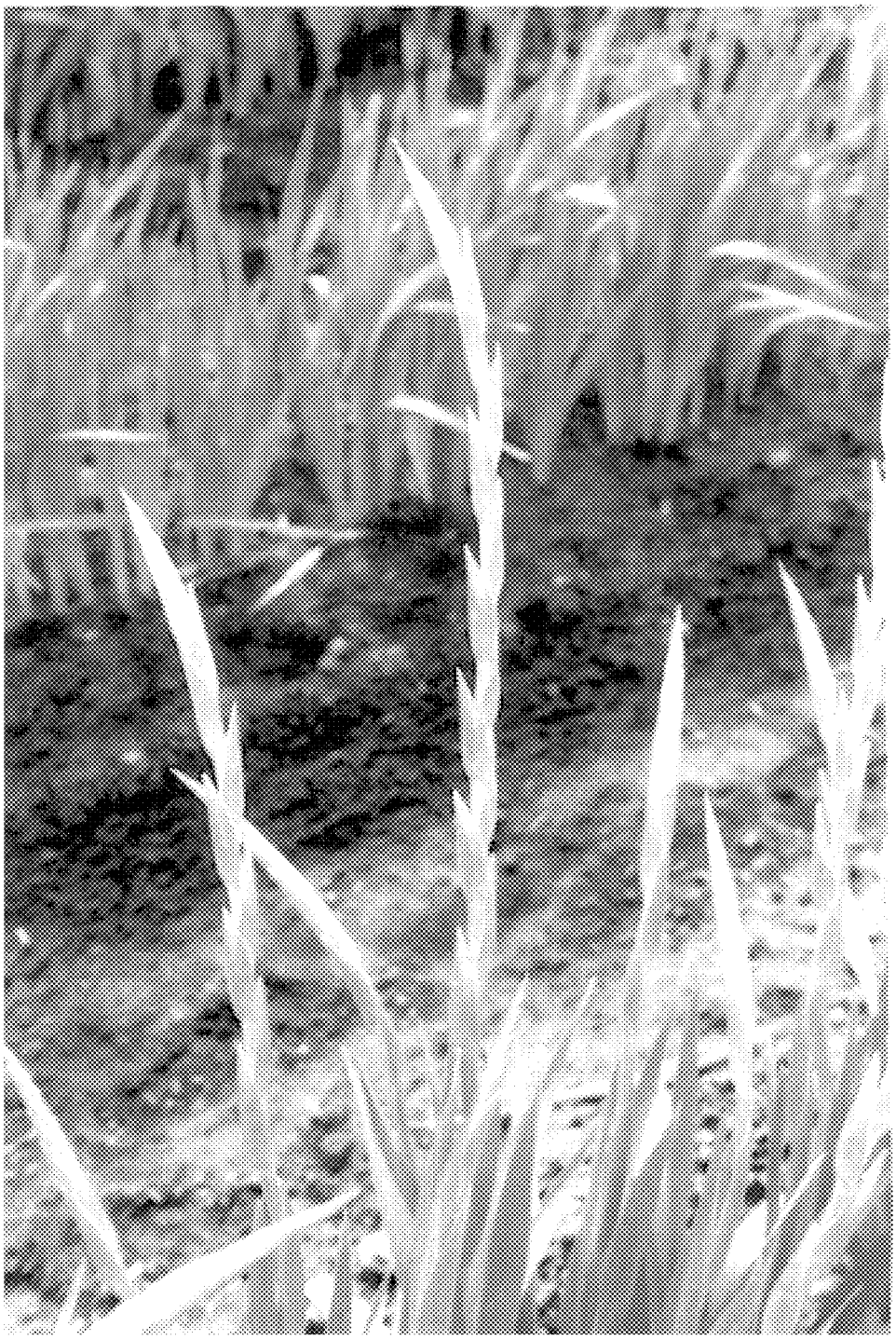
FIGS. 2–3 are photographs of the 'Georgia Peach' cultivar plant prior to blooming.
Figure 3:
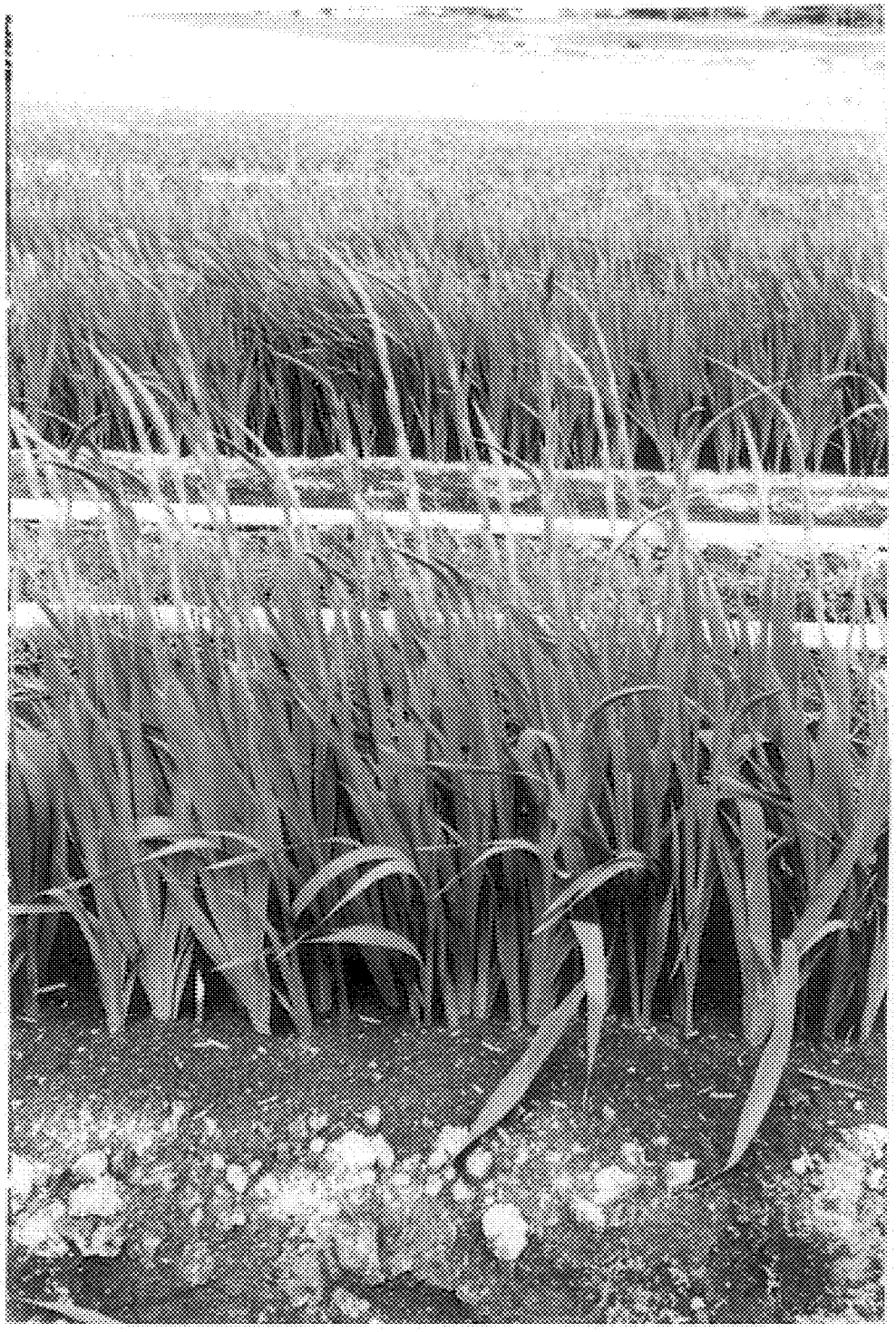

The spike is Green Group 143C on the backside of the stem between the flower bud and normally produces stems of about 125 cm to 130 cm when grown from Jumbo size corms (1.75 inch and larger) in Ecuador. It should be noted, however, that various factors will affect spike length, including temperature (larger spikes occur in cooler weather), irrigation, light intensity, fertilization, soil type (larger spikes occur in heavy soils versus sandy soil), and bulb size (larger bulbs result in larger spikes). The leaf color of the 'Georgia Peach' cultivar is green, namely Green Group 137B on both sides, and tapers to a point with parallel veins running the length of the leaf (FIGS. 2–3). The leaf is typically 4 cm in width and 60 cm in length. The foliage stand fairly straight during growth.

Figure 5:
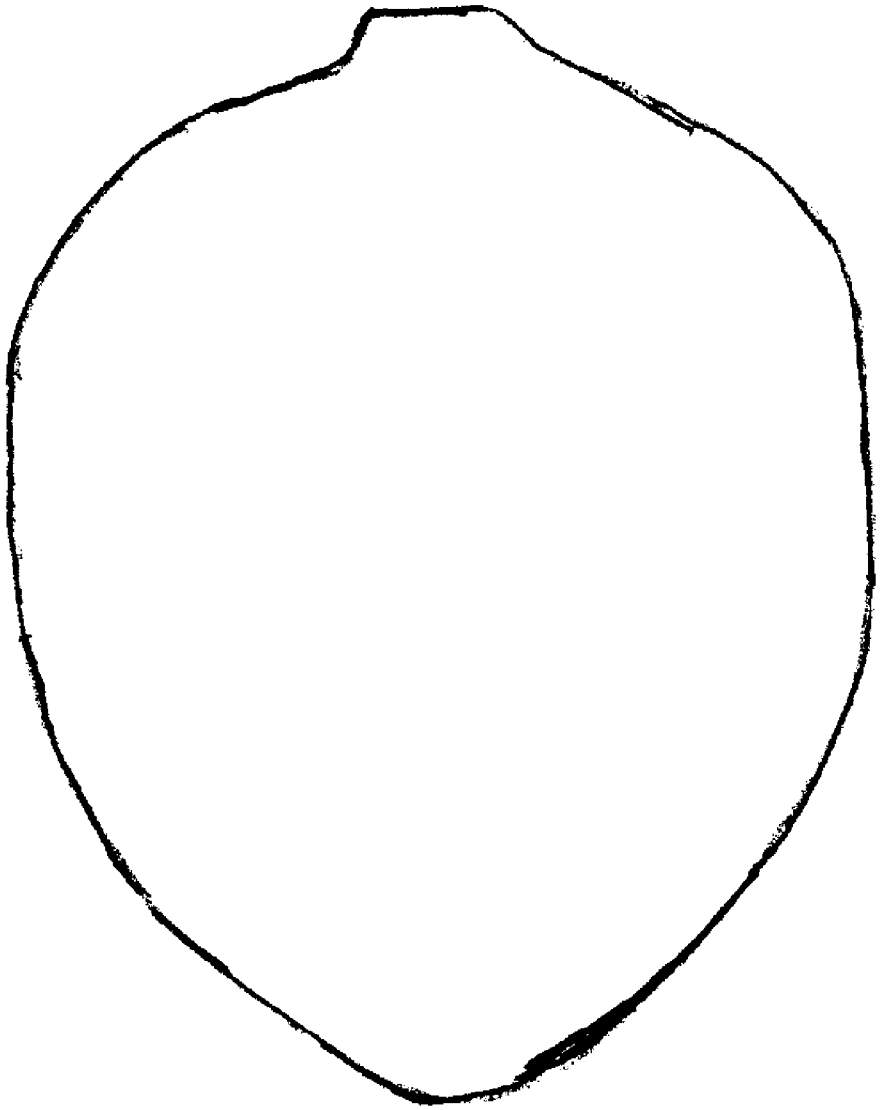
FIG. 5 is a drawing illustrating the shape of the petals.

The bud size of the 'Georgia Peach' cultivar is about 6 cm in length. The flowers of the 'Georgia Peach' cultivar each comprised of six petals, consisting of either five large petals and one small petal, or consisting of four large petals and two small petals, all of which are overlapping. The shape of the petal is illustrated best in FIG. 5, with dimensions of about 2.5 inches in length and about 2 inches in width (at the widest point, then tapering down as shown). The corolla bloom has small marks of red (Red Group 39A) deep within the throat of the bloom. The color of the tight bloom is Red Group 41C. The color of the bloom in open perfect condition is Red Group 43D, with the color of the bloom open going down is Red Group 37C. Small lines run up the middle of each petal. The small petal has a spot of color Red Group 39B. The pistils of the flower are white (pistil head in White Group 155C and pistil stem in White Group 155B. The stamen stem color is White Group 155B, and the stamen head color is Red Purple Group 63D. The diameter of the entire bloom is about 11 cm.

Figure 4:
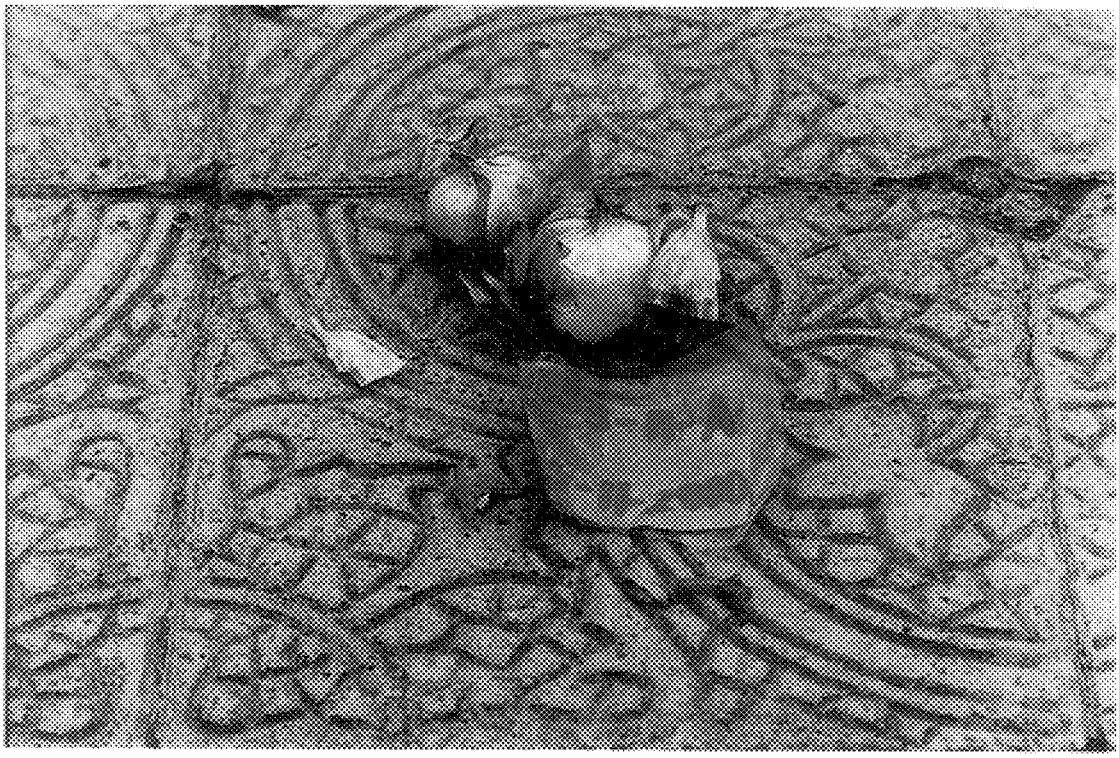
FIG. 4 is a photograph of a corm of the 'Georgia Peach' cultivar plant.

The corms of the 'Georgia Peach' cultivar are typical for the gladiolus and have a Yellow Group 9C color under the husk on top of the bulb one day after harvest (FIG. 4).

General Observations

Compared to the gladiolus variety Dr. Magee (unpatented) the 'Georgia Peach' cultivar produces four to five more flowers per stem, is six to eight inches taller, and will maintain three to four more flowers in open bloom. The 'Georgia Peach' cultivar will, in fact, be able to maintain up to seven to eight flowers in open bloom simultaneously, beginning with a tight cut stem.

The 'Georgia Peach' cultivar does not emit a fragrance.

The cultivar harvests one week faster than the pink variety 'Friendship.'

The 'Georgia Peach' cultivar is very resistant to attack by *Fusarium* and *Curvalaria* fungi species and does not attract worms or red spiders. The 'Georgia Peach' is also tolerant to high temperatures experienced in August through October in Florida as well as temperatures experienced in mid-winter.

The flowers open fast in the field and blooms well under short and long day lengths. The 'Georgia Peach' cultivar stems may be cut tight, shipped dry for a week, and still bloom well.

I claim:

1. A new and distinct gladiolus plant, cultivar 'Georgia Peach', as shown and described herein.

* * * * *

UNITED STATES PATENT AND TRADEMARK OFFICE

CERTIFICATE OF CORRECTION

PATENT NO. : PP 13,990 P3
APPLICATION NO. : 09/745086
DATED : July 22, 2003
INVENTOR(S) : John O. Zipperer, III It is certified that error appears in the above-identified patent and that said Letters Patent is hereby corrected as shown below:

Title Page # 65 of the patent, in the first column under the prior publication data, namely "US 2002/0002721 P1 Jan. 3, 2002", please insert the following: -- Foreign Application Priority Data -- June 9, 2000 (EP) .....2000/0891 --.

Signed and Sealed this

Nineteenth Day of December, 2006

JON W. DUDAS
*Director of the United States Patent and Trademark Office*